United States Patent [19]
Tegeler et al.

[11] Patent Number: 5,804,437
[45] Date of Patent: Sep. 8, 1998

[54] LOCKING STRUCTURE FOR SECURING A FLUID TRANSFER TUBE

[75] Inventors: Garry R. Tegeler, Hazelwood; Kent Smith, St. Charles, both of Mo.

[73] Assignee: bioMérieux Vitek, Inc., Hazelwood, Mo.

[21] Appl. No.: 914,506

[22] Filed: Aug. 19, 1997

[51] Int. Cl.⁶ ................................................... C12M 3/00
[52] U.S. Cl. ..................... 435/287.1; 422/58; 422/102; 435/287.9; 435/288.5; 435/288.7; 435/808
[58] Field of Search ................. 422/58, 102; 435/287.1, 435/287.9, 288.3, 288.5, 288.7, 808

[56] References Cited

U.S. PATENT DOCUMENTS

| | | | |
|---|---|---|---|
| 4,038,151 | 7/1977 | Fadler et al. | 195/127 |
| 4,116,775 | 9/1978 | Charles et al. | 195/103.5 |
| 4,118,280 | 10/1978 | Charles et al. | 195/127 |
| 4,318,994 | 3/1982 | Meyer et al. | 435/301 |
| 5,229,297 | 7/1993 | Schnipelsky et al. | 436/94 |
| 5,609,828 | 3/1997 | O'Bear et al. | 422/102 |
| 5,677,133 | 10/1997 | Oberhardt | 435/7.1 |

*Primary Examiner*—David A. Redding
*Attorney, Agent, or Firm*—McDonnell Boehnen Hulbert & Berghoff

[57] ABSTRACT

A test sample card is provided with a locking feature for achieving a positive, locking engagement with a transfer tube that conducts fluid into the interior of the test sample card. The locking feature consists of a tubular channel inwardly disposed from the fluid intake port that has an inner annular rim defining a restriction. The annular rim is of a reduced diameter relative to the diameter of the transfer tube. A recessed region is positioned inwardly from the restriction that has an opening in one of the surfaces of the card body. When the transfer tube is inserted into the tubular channel, the first end is forced past the restriction into the recessed region, with the annular rim compressing the transfer tube. The user is able to sense with their hands when the first end is inserted past the restriction. Visual observation of the first end of the transfer tube through the opening in the card surface confirms that the transfer tube has been properly inserted into the test sample card.

16 Claims, 4 Drawing Sheets

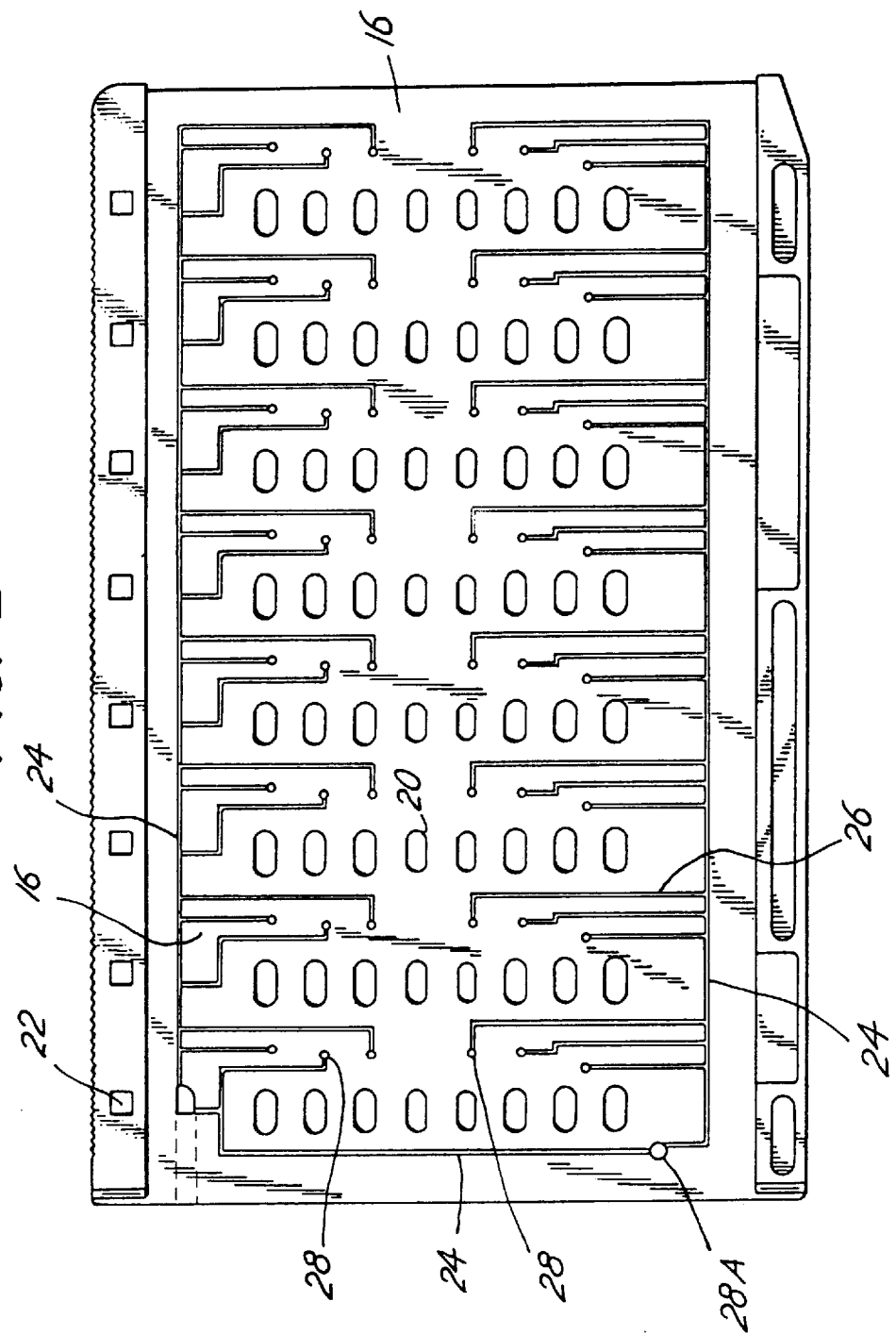

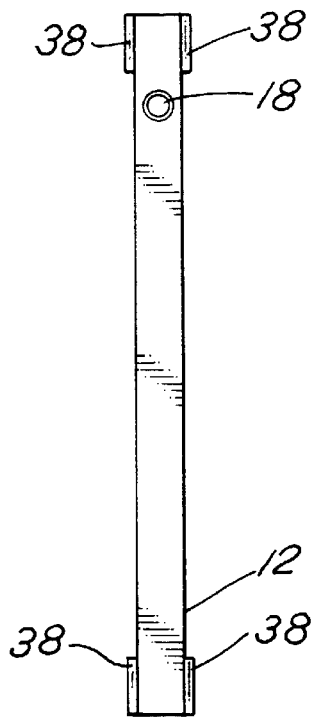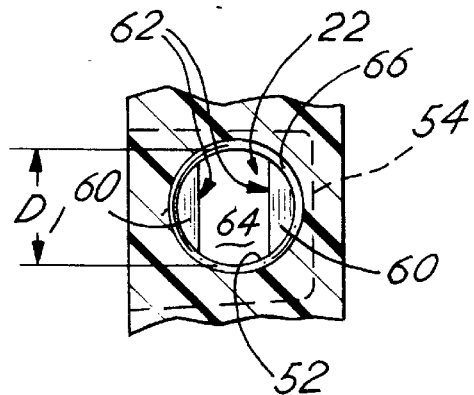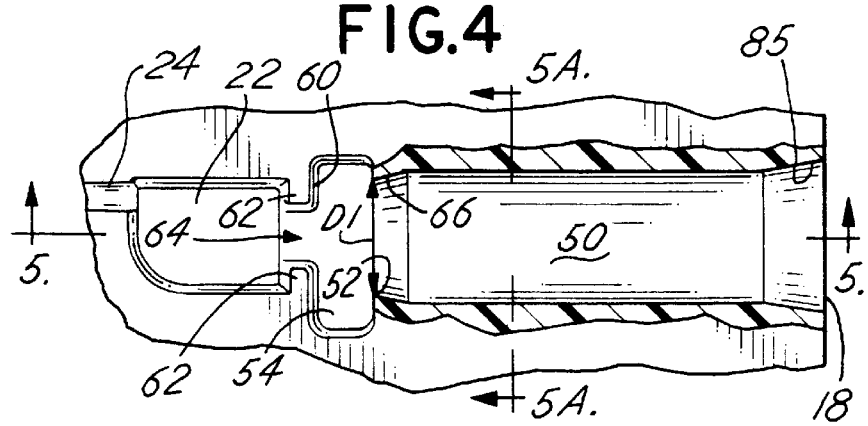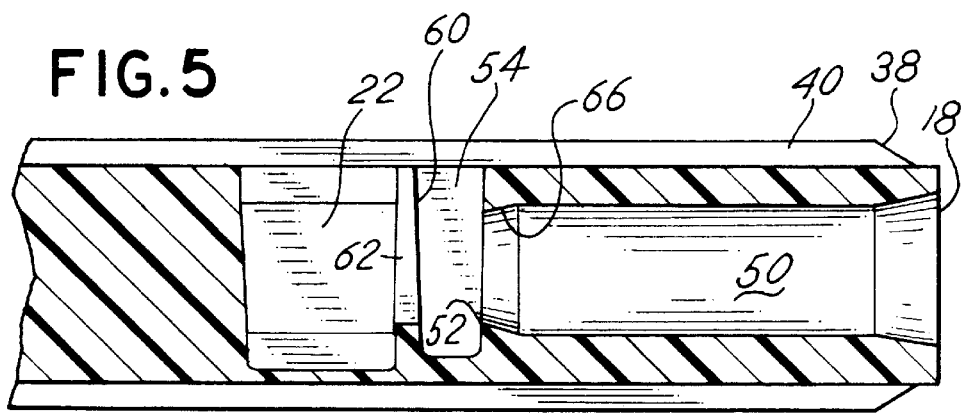

LOCKING STRUCTURE FOR SECURING A FLUID TRANSFER TUBE

BACKGROUND OF THE INVENTION

A. Field of the Invention

This invention relates generally to the field of biological sample testing apparatus and systems, and more particularly to the subject of test sample cards which have one or more wells for containing a fluid or test sample containing a microbiological agent (such as a microorganism) and a reagent, and in which the fluid or test sample is introduced into the card via a straw-like tube known in the art as a transfer tube.

B. Description of Related Art

A variety of test sample cards are described in the patent literature which have a well or reaction site for receiving a fluid sample containing a microbiological agent, such as a microorganism, and a reagent. Several representative patents include Meyer et al., U.S. Pat. No. 4,318,994, Charles et al., U.S. Pat. No. 4,116,775; Fadler et al., U.S. Pat. No. 4,038,151 and Charles et al., U.S. Pat. No. 4,118,280, the contents of each of which are fully incorporated by reference herein. These patents describe a test sample card having a plurality of wells arranged in the test sample card body. The reagent is typically loaded in the wells of the card during the completion of manufacture of the card. The reagent typically comprises a growth medium for a microbiological agent in a fluid or test sample. It is known to load a different reagent in each of the wells of the card in order to perform identification testing of a fluid sample containing an unknown microbiological agent or organism. It is also known to use the cards to test the microbiological agent for susceptibility to the antibiotics by loading various antibiotic reagents into the wells.

In the sample testing system described in the Charles et al '280 patent, after the well of the test sample card has been loaded with the fluid sample, the card is incubated for a period of time to promote a reaction between the microorganism and the reagent, i.e., growth of the microorganism. After a period of time, the well is subject to optical analysis by a transmittance light source and a detector which are positioned on opposite sides of the well or by alternate detection methods. If the growth medium or reagent is specifically suited for or "matches up" with the particular microorganism in the fluid sample, the population of the microorganism increases substantially, or some other predetermined reaction, i.e., chemical reaction, takes place, which results in the well turning cloudy and thus having a change in light transmission characteristics. The detector determines the amount of light that is transmitted from the source through the well. By comparing the transmittance measurement over a period of time, typically several hours at least, with an initial transmittance measurement, it is possible to determine whether in fact the reagent and microbiological agent are matched by virtue of the change in transmittance measurement reaching a threshold value, such as 25 or 30 percent. The change in light transmission characteristics therefore can be used to indicate the presence of a specific microorganism in the well. Identification and susceptibility may also be detected by absorbency measurements where a fluorescent agent is provided in the growth medium.

It is known in the art to introduce the fluid sample into the test sample card using a transfer tube and vacuum techniques. One end of the straw-like transfer tube is inserted into an intake port in the test sample card. Typically, this is performed manually by a laboratory technician at the time the test sample card is used. The free end of the transfer tube is then inserted into a receptacle, such as a test tube, that contains the fluid sample. The test tube/fluid sample with transfer tube and test sample card are then placed as a unit within a vacuum chamber. Vacuum is drawn in the chamber and then released. The release of vacuum draws fluid from the receptacle into the fluid passages and wells, loading the wells with fluid.

The present inventors has appreciated that problems have arisen with regards to prior art test sample card and transfer tube arrangements, in that the user may fail to adequately or properly install the transfer tube into the test sample card. When the transfer tube is not properly installed in the card, a potential for air to leak around the transfer tube and into the fluid passages in the test sample card exists. The air is then carried by fluid distribution to the test sample wells, where the air forms small bubbles in the sample wells. Air bubbles in the wells can adversely affect the accuracy of the reading of the wells by the optical system. Thus, the inventors have appreciated that the manner in which the transfer tube is inserted into the test sample card is a important performance issue in terms of the ability of the card and associated optical instrument to perform up to their optimal capability.

The present invention solves the problem of inadequate transfer tube connection to the test sample card and resulting leakage of air into the fluid distribution channels by providing a novel locking arrangement in the test sample card fluid port that insures that the technician has properly inserted the transfer tube into the test sample card.

It is therefore a primary object of the invention to provide a test sample card and transfer tube arrangement that achieves a positive, leak-free, locking engagement between the transfer tube and the test sample card fluid port, thereby ensuring optimal performance of the test sample card and optical reading system.

A second object of the invention is to provide a locking feature in a test sample card that is easy to use by the technician, and enables the technician to install the transfer tube into the test sample card and immediately know, by both visual and tactile means, whether the transfer tube has been correctly and completely installed in the test sample card.

SUMMARY OF THE INVENTION

A test sample card is provided having front and rear surfaces and at least one sample well. The sample well is loaded with a fluid sample from a source of the fluid sample via a transfer tube. The test sample card includes a fluid intake port sized to received a first end of the transfer tube. An elongate tubular channel is connected to the fluid intake port and has a restriction formed therein. The restriction comprises an annular rim of reduced diameter relative to the diameter of the first end of the transfer tube.

An inspection station is positioned inwardly in the test sample card from the restriction. The inspection station comprises a recessed region or chamber sized to receive the first end of the transfer tube after the first end has been inserted past the restriction. The chamber is ideally open to at least one of the front and rear surfaces of the test sample card body or otherwise optically clear to thereby allow visual observation of the first end of the transfer tube in the chamber.

In a preferred embodiment, a stop is provided in the test sample card positioned in axial alignment with the fluid intake port and inwardly from the restriction. The stop limits the distance the transfer tube may be inserted into the test sample card, and prevents the first end of the transfer tube from interfering with the distribution of the fluid sample to the sample wells.

When the transfer tube is properly inserted into the tubular channel, the first end of the transfer tube is forced past the restriction into the recessed region, with the annular rim compressing the transfer tube to seal off the transfer tube and prevent air bubbles from being introduced into the card. The user is able to sense with their hands when the first end of the transfer tube is inserted past the restriction to reach the stop. Visual observation of the first end of the transfer tube through the opening in the card surface in the inspection station confirms that the transfer tube has been properly inserted into the test sample card.

BRIEF DESCRIPTION OF THE DRAWINGS

A presently preferred embodiment of the invention is described below in conjunction with the appended drawing figures, wherein like reference numerals refer to like elements in the various views, and in which:

FIG. 2 is a plan view of the rear surface of the test sample card of FIG. 1;

FIG. 3 is a side view of the test sample card of FIGS. 1 and 2, showing the intake port that receives the transfer tube;

FIG. 4 is a plan view of the intake manifold, inspection station, and intake port of the card of FIGS. 1–3, shown greatly enlarged and partially broken away in order to illustrate the locking features of the present invention;

FIG. 5 is a cross-sectional view of the intake manifold, inspection station, and intake port of the card of FIG. 4 along the lines 5—5 of FIG. 4, also shown greatly enlarged;

FIG. 5A is an elevational view of the locking annular rim and channel of FIG. 4, shown greatly enlarged, taken along the lines 5A—5A of FIG. 4;

DETAILED DESCRIPTION OF THE PREFERRED EMBODIMENT

Figure 1:
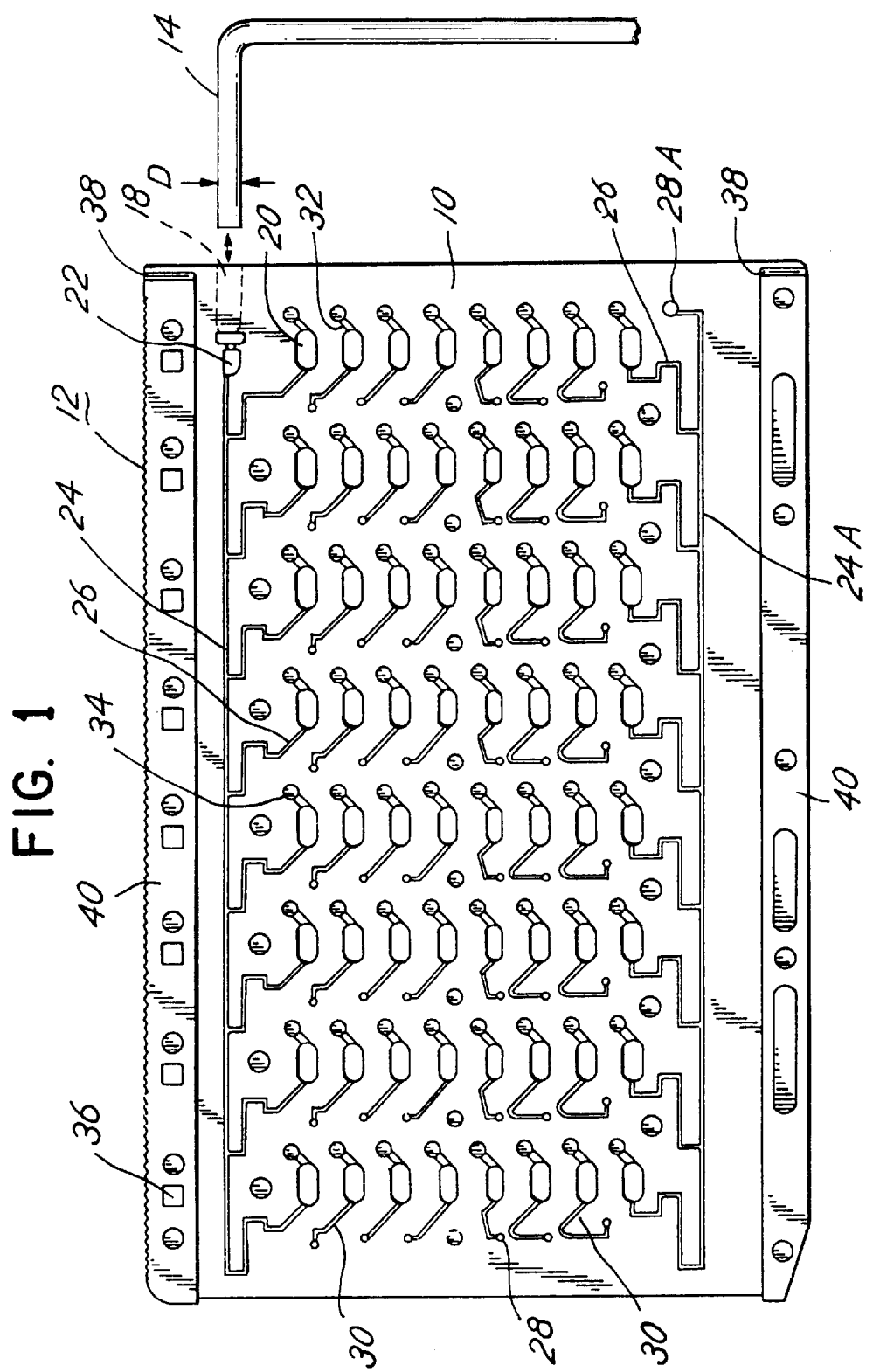
FIG. 1 is a plan view of the front surface of a test sample card incorporating features for locking a transfer tube to the test sample card.

Referring now to FIG. 1, the front surface 10 of a test sample card 12 is shown in a plan view. The test sample card 12 incorporates the present locking features for locking a straw-like transfer tube 14 to the test sample card 12. FIG. 2 is a plan view of the opposite rear surface 16 of the test sample card 12 of FIG. 1. FIG. 3 is a side view of the test sample card of FIGS. 1 and 2, showing the intake port 18 that receives the transfer tube 14.

Before discussing the locking feature of the card 12 per se, other features of the test sample card that are apparent in FIGS. 1–3 will be addressed briefly. The test sample card 12 includes a plurality of sample wells 20 arranged in an array of rows and columns of wells. The wells 20 are pre-loaded with reagents and/or growth media for fluid or test samples. The fluid or test sample is loaded into the card 12 by means of vacuum loading techniques known in the art. After a transfer tube 14 is inserted into the fluid intake port 18 and locked in place in the manner described below, the fluid is drawn through the transfer tube 14 to an intake manifold 22 that supplies fluid distribution channels 24 positioned on both the front and rear surfaces of the test sample card body. The fluid is carried along the fluid channels 24 to secondary supply channels 26 that lead to the sample wells 20. Through-card fluid distribution channels 28 and 28A are provided for supplying fluid from the rear supply channels to well supply channels 30 and fluid distribution channel 24A, respectively, on the front surface 10 of the card 12.

The sample wells 20 are in communication with bubble trap passages 32 that convey any air bubbles that may form in the well to a respective bubble trap 34 (FIG. 1). Any air bubbles that may be present in the wells as a by product of a test reaction or by fluid distribution tend to migrate to the bubble traps 34, either by virtue of manual jiggling of the card or as a consequence of jostling or tumbling of the card during processing or incubation of the card in an analytical instrument.

The wells 20, bubble traps 34, sensor stop holes 36, and many other features, such as the ramp 38 and raised rail features 40, that are not specifically related to the present locking feature for the transfer tube are described in greater detail in the patent to Raymond E. O'Bear et al., U.S. Pat. No. 5,609,828, assigned to the assignee of the present invention, which is fully incorporated by reference herein. Additionally, the front and rear surfaces of the card 12 are preferably covered with a transparent, high oxygen permeable and transmissible adhesive membrane as described in the patent application of Patrick Chen et al., application Ser. No. 08/455,404 filed May 31, 1995. The reader is directed to the above '828 and patents for a detailed discussion of these features and still other features of the card 12.

Figure 6:
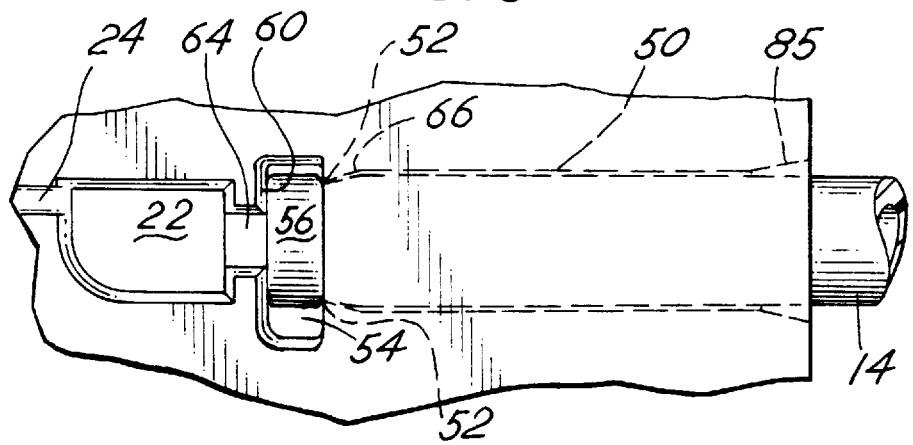
FIG. 6 is a plan view of the intake manifold, inspection station, and intake port of the card of FIGS. 1–3, with a transfer tube inserted into the intake port with the end thereof visible through the inspection station, with a portion of the intake port and transfer tube shown in dashed lines in order to indicate their position within the card body between the front and rear surfaces of the card body.

The particular locking feature of the present invention consists of a feature that is located in the upper right hand portion of the illustrated card 12 in FIG. 1 in the internal card structure between the fluid intake port 18 and the intake manifold 22, and this feature will be more particularly described in conjunction with FIGS. 4–7. The port and locking feature on a test sample card may be at other locations on the test sample card body such as in the cards shown in the above-referenced Charles et al. patents. The locking feature is applicable to other fluid connections which utilize a fluid transfer tube. FIG. 4 is a plan view of the intake manifold 22, a visual inspection station 54, intake port 18 and an elongate tubular channel 50 of the card of FIGS. 1–3, shown greatly enlarged and partially broken away in order to illustrate the locking features of the present invention. FIG. 5 is a cross-sectional view of the intake manifold 22, inspection station 54, channel 50 and intake port 18 along the lines 5—5 of FIG. 4, also shown greatly enlarged. FIG. 5A is an elevational view of the innermost end of the channel 50 showing the annular rim 52 that locks the transfer tube 14, and the channel 64 between two opposed wall portions 62 that allows fluid to be conducted from the transfer tube into the intake manifold 22. FIG. 6 is a plan view of the intake manifold 22, inspection station 54, and intake port 18 of the card of FIGS. 1–3, with a transfer tube 14 inserted into the intake port 18 with the first end 56 thereof visible through the inspection station 54. The terminal end wall of the fluid transfer tube butts against the stop 60 of the inspection station 54. In FIG. 6, the elongate tubular channel 50 and a portion of the transfer tube 14 are shown in dashed lines in order to indicate their position within the interior of the card 12 between the front and rear surfaces of the card 12.

Referring to these figures, the locking feature in a preferred embodiment comprises a tubular channel 50 in communication with the fluid intake port 18 that has an annular rim 52 of reduced diameter relative to the channel 50 and transfer tube 14 that forms a restriction disposed at one end thereof opposite the fluid intake port 18. The walls of the channel 50 are sized to accommodate the first end of the transfer tube and guide it towards the frusto-conical taper section 66 and the annular restriction 52. The restriction 52 has a first diameter D1, wherein D1 is slightly less than the outside diameter D of the first end of the transfer tube 14, and less than the diameter of the main body of the tubular channel 50. A recessed region forming a chamber 54 is provided that is disposed in axial alignment with the fluid intake port 18 and positioned inwardly in the test sample card from the restriction 52. In a preferred embodiment, the recessed chamber 54 is sized to accommodate the first end 56 of the transfer tube 14 after the first end has been inserted past the restriction 52, as shown in FIG. 6. The recessed chamber 54 is preferably formed as an opening in either the front 10 or the rear 16 surface of the test sample card 12 (or perhaps both), or is otherwise optically clear, so as to provide an inspection station for visually observing whether the first end 56 of the transfer tube 14 has been properly and fully inserted into the test sample card. In the embodiment of FIG. 1, the opening for the recessed chamber 54 is formed in the front surface 10 of the test sample card 12. The chamber 54 is covered by the transparent adhesive membrane after completion of manufacture of the card, as are the wells, the manifold 22, and the fluid channels in the front and rear card surfaces.

A stop 60 is provided comprising a pair of walls 62 separated by a vertical gap 64 (see FIGS. 4 and 5A) axially aligned with the fluid intake port 18 and channel 50 inwardly from the restriction 52 relative to the intake port 18. The vertical gap or channel 64 is sized so as to be equal to or slightly greater than the diameter of the internal fluid passageway in the transfer tube 14 so as to not obstruct the flow of fluid from the transfer tube into the manifold 22.

The stop 60 limits the distance the transfer tube 14 may be inserted into the test sample card 12. Further, the stop 60 acts to prevent the transfer tube 14 from obstructing the intake manifold 22 and interfering with the proper distribution of the fluid sample to the wells in the card. In a preferred embodiment, the stop 60 is positioned such that the first end of the transfer tube 14 may be inserted a total distance of between 5 and 7 mm into the test sample card, such that the first end 56 terminates in the visual inspection station 54, and does not enter the intake manifold 22. The channel 50 could be constructed to be somewhat shorter, with a minimum length of the channel 50, including the frusto-conical taper section 66, being about 2 mm. Thus, a preferred length for the channel 50 is between 2 and about 7 mm. A 1 mm deep frusto-conical tapered entrance 85 with a 20 degree draft angle is provided which assists the user in inserting the transfer tube into the port 18. Further, in an alternative embodiment, the entire channel 50 could be one continuous tapering of the channel walls leading to the annular restriction 52.

When the transfer tube 14 is being inserted into the intake port 18 such that the first end 56 abuts the restriction 52, the user perceives a noticeable increase in the resistance or force required to insert the transfer tube 14 further, owing to the fact that the diameter of the transfer tube 14 is greater than the diameter of the restriction 52 and an interference or compression of the transfer tube 14 occurs. When the user pushes slightly harder on the transfer tube 14 to further insert the transfer tube 14 past the restriction 52, additional force is required to deform the first end 56 of the transfer tube 14 slightly and force it past the restriction. A tapering of the channel 50, such as by providing a frustoconical region 66 in the inner portion of the channel 50 leading to the restriction 52, assists in compressing the transfer tube 14, without substantially restricting the internal fluid passageway of the transfer tube 14. As the first end of the transfer tube 14 is moved past the restriction 52 and into the recessed chamber 54, a substantial decrease in insertion force needed to move the transfer tube further inward is again noticed in the hands of the user. The first end 56 of the transfer tube 14 expands to its original diameter (due to the elastic nature of the plastic transfer tube). The first end 56 is constrained in the recessed region or chamber 54 by means of the stop 60 and the restriction 52, and is visually observed by the opening in the surface of the card above the chamber 54.

The retention of the first end 56 of the transfer tube 14 by the restriction 52 (as shown in FIG. 6) essentially locks the transfer tube 14 to the test sample card 10, such that the transfer tube 14 substantially resists pull out forces that may be ordinarily imparted to the transfer tube. Moreover, by virtue of the elastic deformation of the transfer tube 14 by the restriction 52 and tight, compressive, positive engagement of the restriction 52 and the transfer tube 14 body, an effective seal is created between the exterior surface of the transfer tube 14 and the annular restriction 52, preventing air from entering into the interior of the card and being distributed to the wells and interfering with the reading of the wells of the card.

Figure 7:
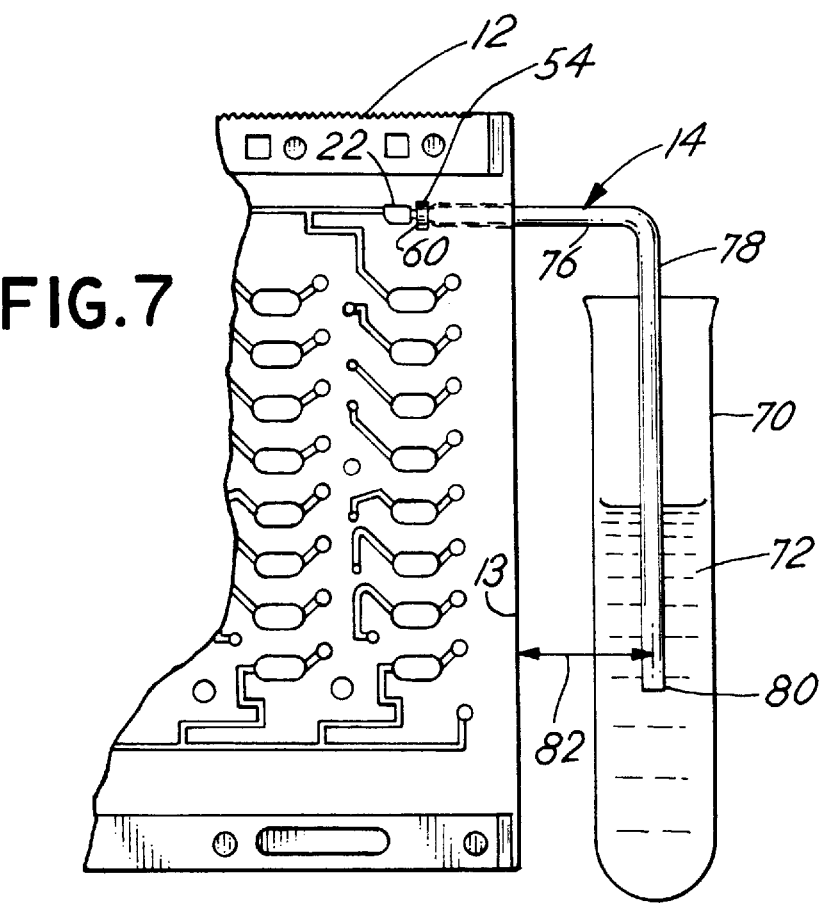
FIG. 7 is an elevational view of the test sample card of FIGS. 1–3 in an assembled condition with a transfer tube, with the free end of the transfer tube inserted into a test tube containing a fluid sample that is to be loaded into the test sample card.

FIG. 7 is an elevational view of the test sample card of FIGS. 1–3 in an assembled condition with a transfer tube 14, with the free end of the transfer tube 14 inserted into a test tube 70 containing a fluid sample 72 that is to be loaded into the test sample card 12. Note the presence of the first end of the transfer tube in the visual detection station 54, indicating that the transfer tube 14 is properly inserted into the test sample card.

The transfer tube 14 is preferably made from a smooth, deformable plastic material. In the illustrated embodiment, the transfer tube has a nominal diameter D of 2 mm, and the restriction diameter D1 is 1.956 mm, but these dimensions could be increased or decreased, along with a proportional increase or decrease in the diameter of the channel 50 form a nominal diameter of 2.138 mm. A preferred composition for the transfer tube is a mixture of 74% low density polyethylene, 24% high density polyethylene, and 2% color agent. This mixture gives a transfer tube with the proper harness and resiliency for the illustrated embodiment. Other materials may be suitable for the transfer tube, particularly low durometer plastics or blends of such materials, for example polypropylene or various grades thereof. The transfer tube need not have any features at the first end to work with the locking structure in the test sample card body, and may be smooth.

The distance the transfer tube is inserted into the test sample card is not particularly important, but as noted above, the locking annular rim 52 should be located at least 2 mm inside the opening 18 the card. Referring to FIG. 7, the position of the stop 60 together with the length of the upper region 76 of the "L" shape in the transfer tube controls the position of the downward depending portion 78 and free end 80 of the transfer tube 14 relative to the side 13 of the card body. In some applications, this distance 82 may be important, and the appropriate dimensions should be provided in the portion 76 of the transfer tube, taking into account the distance the first end of the transfer tube is inserted into the card.

A preferred analytical instrument for loading the card 12 with the fluid sample via the transfer tube using vacuum, incubating the card, and conducting optical analysis of the wells of the card of FIGS. 1–7 is set forth in the patent application of Mark J. Fanning et al., application Ser. No. 08/604,672, filed Feb. 21, 1996, which is fully incorporated by reference herein.

We have thus described a testing apparatus comprising a transfer tube 14 having a first end and a second end and a test sample card 12 having at least one well 20 for receiving a fluid sample and a fluid intake port 18 formed in an exterior surface of the card. The fluid sample is loaded into the test sample card by means of the transfer tube 14. The first end 56 of the transfer tube 14 is for insertion into the fluid intake port 18 and the second free end is for placement into a receptacle in contact with said fluid sample, for example in the manner shown in FIG. 7. The first end 56 of the transfer tube 14 has an outside diameter D. The test sample card further comprises an elongate tubular channel 50 in communication with the fluid intake port 18 having an inner annular rim 52 thereof defining a restriction of a diameter D1, wherein D1<D. A recessed region 54 is provided that is disposed in axial alignment with the fluid intake port 18 and positioned inwardly in the test sample card 12 from the annular rim 52. The recessed region 54 is sized to receive the first end of the transfer tube 14 (as shown in FIG. 6) after insertion of the first end of the transfer tube past the annular rim 52. The annular rim 52 cooperates with the first end of the transfer tube by providing a squeezing, interference fit to promote the retention of the transfer tube and test sample card in an assembled condition when the first end of the tube has been inserted into the intake port and into the recessed region or inspection station 54.

The recessed region 54 preferably comprises an opening in a surface of the test sample card body thereby providing an inspection station permitting visual observation of the first end of the transfer tube 14.

It will also be appreciated that a method for securing a tubular-shaped transfer tube 14 into a fluid intake port 18 is set forth herein, comprising the steps of:

a) inserting a first end of the transfer tube 14 into the fluid intake port 18;

b) pushing the transfer tube 14 further into the fluid intake port 18 until the first end 56 of the transfer tube 14 makes contact with a restriction 52 within the fluid intake port 18, the restriction comprising an annular rim of reduced diameter relative to the diameter of the first end of the transfer tube;

c) urging the first end of the transfer tube past the restriction 52 into a recessed region 54 in axial alignment with the fluid intake port 18 and the restriction 52, with the recessed region 54 having a diameter greater than or equal to the diameter of said first end of said transfer tube 14 to thereby accommodate the first end of the transfer tube 14 after it has expanded to substantially its original diameter; and d) observing through a window in test sample card (formed in one embodiment by covering the opening in the recessed region 54 with a transparent adhesive tape) whether the first end of the transfer tube 14 has been inserted in the recessed region 54, with the presence of the first end of the transfer tube in the recessed region or inspection station 54 indicating that the transfer tube 14 has been inserted properly into the test sample card 12.

In the event that the test sample card further comprises an intake manifold in axial alignment with the restriction, the method preferably further comprises the step of stopping the insertion of the transfer tube 14 at a predetermined location with a stop 60 so that the transfer tube 14 does not enter the intake manifold and interfere with the distribution of the fluid sample through the intake manifold 22 to the wells 20.

As noted above, a presently preferred test sample card for use with the invention is described in the patent to Raymond E. O'Bear et al., U.S. Pat. No. 5,609,828, which is incorporated by reference. However, the invention is of course suitable for use with many other types of test sample cards, for example, the test sample cards described in the Background of the Invention section, supra, and in other similar types of fluid connection devices. The particular details as to the number, size, shape and arrangement of sample wells, the configuration of the fluid distribution channels, and so on, are not particularly important to the inventive transfer tube locking feature described herein.

Persons of skill in the art will appreciate that variation may be made to the preferred embodiment described above without departure from the true spirit and scope of the invention. This true spirit and scope is determined by the appended claims, to be interpreted in light of the foregoing.

We claim:

1. In a test sample card comprising at least one well for receiving a fluid sample and a fluid intake port formed in an exterior surface of said card, said fluid sample loaded into said test sample card by means of a transfer tube having a first end received in said fluid intake port and a second free end for placement into a receptacle in contact with said fluid sample, said transfer tube having an outside diameter D, an improvement in said test sample card comprising:

a tubular channel in communication with said fluid intake port having a restriction disposed at one end thereof opposite said fluid intake port, said restriction defining a first diameter D1, wherein D1 is less than D;

a recessed region disposed in axial alignment with said fluid intake port and positioned inwardly in said test sample card from said restriction, said recessed region for receiving said first end of said transfer tube after said first end has been inserted past said restriction; and a stop positioned in axial alignment with said fluid intake port and recessed region positioned inwardly from said restriction, said stop limiting the distance said transfer tube may be inserted into said test sample card;

whereby said restriction cooperates with said first end of the transfer tube to securely and sealingly engage said transfer tube to said test sample card.

2. The improvement of claim 1, wherein said transfer tube is made from a deformable plastic material.

3. The improvement of claim 1, wherein said stop is positioned within said test sample card such that said first end of said transfer tube may be inserted a total distance of at least 2 mm into said test sample card.

4. The improvement of claim 1, wherein said recessed region further comprises an opening in said test sample card body or an optically clear region permitting visual observation of said first end of said transfer tube when said transfer tube has been inserted past said restriction.

5. The improvement of claim 1, wherein said restriction comprises a tapered, frusto-conical surface in said tubular channel having an innermost rim defining said first diameter D1.

6. The improvement of claim 1, wherein said restriction cooperates with said transfer tube to provide a sealing engagement therebetween preventing air from entering into said test sample card between said transfer tube and said restriction.

7. Sample testing apparatus, comprising, in combination, a transfer tube having a first end and a second end;

a test sample card having at least one well for receiving a fluid sample and a fluid intake port formed in an exterior surface of said card, said fluid sample loaded into said test sample card by means of said transfer tube; said first end of said transfer tube for insertion in said fluid intake port and said second free end for placement into a receptacle in contact with said fluid sample, said first end of said transfer tube having an outside diameter D, said test sample card further comprising:
(a) an elongate tubular channel in communication with said fluid intake port having an inner annular rim thereof defining a first diameter D1, wherein D1<D;
(b) a recessed region disposed in axial alignment with said fluid intake port and positioned inwardly in said test sample card from said annular rim of said tubular channel, said recessed region sized to receive said first end of said transfer tube after insertion of said first end of transfer tube past said annular rim,
(c) said annular rim cooperating with said first end of said transfer tube to promote the retention of said transfer tube and test sample card in an assembled condition when said first end of said transfer tube has been inserted into said intake port and into said recessed region.

8. The apparatus of claim 7, wherein said test sample card further comprises a stop positioned in axial alignment with said fluid intake port and recessed region positioned inwardly from said recessed region, said stop limiting the distance said transfer tube may be inserted into said test sample card.

9. The apparatus of claim 7, wherein said transfer tube is made from a deformable plastic material.

10. The apparatus of claim 8, wherein said stop is positioned within said test sample card such that said first end of said transfer tube may be inserted a total distance of between 4 and 8 mm into said test sample card.

11. The apparatus of claim 7, wherein said recessed region further comprises an opening in said surface of said test sample card body or an optically clear region thereby providing an inspection station permitting visual observation of said transfer tube when said transfer tube has been inserted into said tubular channel such that said first end thereof has been inserted past said annular rim.

12. A test sample card having front and rear surfaces and at least one sample well, said sample well loaded with a fluid sample from a source of said fluid sample via a transfer tube, comprising:

a fluid intake port sized to received a first end of said transfer tube;

a tubular channel connected to said fluid intake port and having a restriction formed therein, said restriction comprising a region of reduced diameter relative to the diameter of said first end of said transfer tube;

an inspection station positioned inwardly in said test sample card from said restriction, said inspection station comprising a chamber sized to receive said first end of said transfer tube after said transfer tube has been inserted past said restriction, wherein said chamber is open to at least one of said front and rear surfaces of said test sample card body or optically clear to thereby allow visual observation of said first end of said transfer tube in said chamber.

13. The test sample card of claim 12, further comprising a stop positioned in axial alignment with said fluid intake port and positioned inwardly from said restriction, said stop limiting the distance said transfer tube may be inserted into said test sample card.

14. The test sample card of claim 12, wherein said transfer tube is made from a deformable plastic material.

15. The test sample card of claim 13, wherein said stop is positioned within said test sample card such that said first end of said transfer tube may be inserted a total distance of at least 2 mm into said test sample card.

16. The test sample card of claim 12, wherein said restriction comprises a tapered, surface in said tubular channel having an innermost rim defining said region of reduced diameter.

* * * * *